United States Patent
Wei et al.

(10) Patent No.: US 12,257,584 B2
(45) Date of Patent: Mar. 25, 2025

(54) BIOCHEMICAL REACTION TEST STRIP TUBE AND USE METHOD THEREOF, AND KIT

(71) Applicants: QUICKING BIOTECH CO., LTD., Shanghai (CN); QUICKING BIOENGINEERING CO., LTD., Shanghai (CN)

(72) Inventors: Li Wei, Shanghai (CN); Xianghua Xu, Shanghai (CN); Zhongren Zhou, Shanghai (CN)

(73) Assignees: QUICKING BIOTECH CO., LTD., Shanghai (CN); QUICKING BIOENGINEERING CO., LTD., Shanghai (CN)

( * ) Notice: Subject to any disclaimer, the term of this patent is extended or adjusted under 35 U.S.C. 154(b) by 810 days.

(21) Appl. No.: 17/310,810

(22) PCT Filed: Feb. 25, 2020

(86) PCT No.: PCT/CN2020/076667
§ 371 (c)(1),
(2) Date: Aug. 25, 2021

(87) PCT Pub. No.: WO2020/173446
PCT Pub. Date: Sep. 3, 2020

(65) Prior Publication Data
US 2022/0161253 A1    May 26, 2022

(30) Foreign Application Priority Data

Feb. 25, 2019 (CN) .................. 201920239234.X
Feb. 24, 2020 (CN) .................. 202010114034.9

(51) Int. Cl.
*B01L 3/00* (2006.01)
*B01L 7/00* (2006.01)
(Continued)

(52) U.S. Cl.
CPC ............ *B01L 3/50825* (2013.01); *B01L 7/52* (2013.01); *B01L 2200/0689* (2013.01);
(Continued)

(58) Field of Classification Search
CPC ....... B01L 2200/0689; B01L 2300/042; B01L 2300/043; B01L 2300/069;
(Continued)

(56) References Cited

U.S. PATENT DOCUMENTS

2003/0162285 A1* 8/2003 Tajima ................ B01L 3/50851
435/303.1
2004/0110167 A1* 6/2004 Gerdes ................ C12Q 1/6834
436/514
(Continued)

FOREIGN PATENT DOCUMENTS

CN       101906385 A     12/2010
CN       201817488 U      5/2011
(Continued)

OTHER PUBLICATIONS

China National Intellectual Property Administration, International Search Report, International Application No. PCT/CN2020/076667, Mailed May 11, 2020, 6 Pages.

*Primary Examiner* — Jennifer Wecker
*Assistant Examiner* — Jonathan Bortoli
(74) *Attorney, Agent, or Firm* — Ziegler IP Law Group, LLC.

(57) ABSTRACT

The present application relates to a biochemical reaction test strip tube and a use method thereof, and a kit. The biochemical reaction test strip tube includes a tube portion and a cover portion. The tube portion includes: a tube body including a first chamber and a second chamber; a limit unit provided at an outer side of the tube body; and a biochemical chromatographic test strip provided inside the second cham-
(Continued)

ber, where a first end of the biochemical chromatographic test strip is provided with a sample absorption pad. In this structure, different chambers are provided in the closed test tube, such that a biochemical reaction solution in one chamber is directly detected on the biochemical chromatographic test strip in another chamber, which avoids the solution leakage; and different chambers are provided at different heights, such that the chambers holding biochemical reaction reagents can be selectively heated.

16 Claims, 7 Drawing Sheets

(51) Int. Cl.
  *C12Q 1/686* (2018.01)
  *G01N 33/543* (2006.01)
(52) U.S. Cl.
  CPC ... *B01L 2300/042* (2013.01); *B01L 2300/043* (2013.01); *B01L 2300/069* (2013.01); *B01L 2300/0825* (2013.01); *B01L 2300/0832* (2013.01); *B01L 2300/1805* (2013.01); *C12Q 1/686* (2013.01); *G01N 33/54388* (2021.08)
(58) Field of Classification Search
  CPC ..... B01L 2300/0825; B01L 2300/0832; B01L 2300/1805; B01L 3/50825; B01L 7/52; B01L 2300/0609; B01L 2300/0663; B01L 3/502; C12Q 1/686; C12Q 2565/625; G01N 33/52; G01N 33/54388; G01N 33/558

See application file for complete search history.

(56) References Cited

U.S. PATENT DOCUMENTS

| | | | |
|---|---|---|---|
| 2010/0064781 A1* | 3/2010 | Cherubini | B01L 3/50851 73/863.11 |
| 2011/0031252 A1* | 2/2011 | Pack | B01L 3/5025 220/507 |
| 2012/0055626 A1* | 3/2012 | Bhullar | G01N 27/3272 156/250 |
| 2019/0250075 A1* | 8/2019 | Wu | A61B 10/0051 |

FOREIGN PATENT DOCUMENTS

| | | |
|---|---|---|
| CN | 202920244 U | 5/2013 |
| CN | 103243087 A | 8/2013 |
| CN | 205574438 U | 9/2016 |
| CN | 106061612 A | 10/2016 |

* cited by examiner

BIOCHEMICAL REACTION TEST STRIP TUBE AND USE METHOD THEREOF, AND KIT

CROSS REFERENCE TO RELATED APPLICATION(S)

This patent application is a national stage application of PCT/CN2020/076667 filed on Feb. 25, 2020, which claims the benefit and priority of Chinese Patent Application No. 201920239234.X filed on Feb. 25, 2019, and Chinese Patent Application No. 202010114034.9, filed on Feb. 24, 2020, the disclosure of which is incorporated by reference herein in its entirety as part of the present application.

TECHNICAL FIELD

The present disclosure relates to the technical field of bioengineering, and in particular to a biochemical reaction test strip tube and a use method thereof, and a kit.

BACKGROUND

For a conventional small-scale biochemical reaction, one chamber is generally provided in a single test tube to accommodate one kind of solution. When multiple kinds of solutions are required for a reaction, the solutions in different test tubes are drawn out and added to a new test tube, and a final reaction solution is placed in a specific detection device, where a reaction result is determined according to a reaction signal. In order to determine a reaction result more simply, a biochemical test strip is generally used for signal detection of a reaction solution, in which case, the reaction solution needs to be drawn out and added dropwise on the test strip. Due to some special reasons such as reagent contamination, a test tube holding a solution needs to be kept tightly closed, and the solution is not allowed to be drawn out and added dropwise on a test strip for detection, such as anthrax pathogen detection, dioxin detection, and other items.

Since Cetus in the United States used polymerase chain reaction (PCR) to achieve specific nucleic acid amplification (NAA) in 1985, the PCR technology has been widely used in the detection of disease pathogens due to its high sensitivity, high specificity, and high efficiency. However, an amplified high-concentration pathogenic nucleic acid sequence can easily pollute the air, test instruments, and water during subsequent operations, which may lead to false positive results for subsequent test samples. Therefore, for the popularization of nucleic acid detection, it is also necessary to develop closed detection devices and methods. Gerdes, et al. (US2004/0110167) used lateral flow immunochromatographic assay (LFIA) to the detection of NAA products, which brought hope to the application of nucleic acid detection at the grassroots level. In order to avoid contamination during a nucleic acid LFIA process, a device is optimally used to make the chromatographic process proceed in a closed environment. Gu Jiayong, et al. (CN1888902) invented a fully-closed device for rapidly detecting a target NAA product. The device has a structure including an outer housing and an inner box, and the inner box includes a chromatography diluent, an NAA product, and a chromatographic test strip, where when the outer housing is closed, a blade in the inner box pierces a diluent tube and an NAA tube, and the two liquids are mixed and introduced to a sample pad of the chromatographic test strip to realize an immunochromatographic chromogenic reaction. However, the device has the following disadvantages: 1. The device is large in size, which is not suitable for mass production and transportation of a finished product. 2. The installation of a test strip in the device is complicated, which is not suitable for large-scale assembly production of the test strip. 3. The device, after being started and used, can be reopened easily without traces, so the NAA product is relatively closed. The unintentional opening of a reacted device will inevitably cause contamination due to an amplification product. 4. The device can only complete the detection of a single reaction solution, but cannot detect multiple reaction solutions, that is, the device cannot complete the detection of multiple samples on one test strip through multiple reaction solutions.

Chinese patent CN103529201A discloses a closed chromatographic test strip detection device, which can achieve complete closure and can completely prevent the operator hazard and environmental pollution caused by a sample on a chromatographic test strip. However, the device has the following disadvantages: 1. When a solution tube has a small diameter, a bottom of the solution tube is difficult to open. 2. A gas in a connecting tube is not easy to enter a solution tube, causing a gas pressure in the connecting tube to increase. If a gas pressure in the connecting tube exceeds a gas pressure outside the tube and a pressure difference exceeds a bearing pressure of a sealing structure, the gas in the tube will be discharged outside, and when there is a solution in the tube, the solution will leak under the driving of the gas.

Chinese patent 201310157026.2, 201610143977.8, and 201310511291.6 disclose devices where a solution is introduced from a pierced bottom of a test tube into a closed chamber through the cooperation of the reaction test tube with the closed chamber holding a chromatographic test strip. However, the device has the following disadvantages: The device is composed of multiple parts and also requires additional actions and parts to pierce a bottom of the reaction test tube. When a bottom of the reaction test tube is pierced, due to air pressure and other reasons, a seal must be kept between the reaction test tube and the closed chamber to prevent solution leakage, which requires an operator to have appropriate operating skills.

SUMMARY OF THE APPLICATION

To overcome the shortcomings in the prior art, the present disclosure provides a biochemical reaction test strip tube and a kit.

To achieve the above objective, the present disclosure adopts the following technical solutions.

In a first aspect of the present disclosure, a biochemical reaction test strip tube is provided, including a tube portion and a cover portion, where the tube portion includes:
  a tube body including a first chamber and a second chamber;
  a limit unit provided at an outer side of the tube body; and
  a biochemical chromatographic test strip placed in the second chamber, where a first end of the biochemical chromatographic test strip is provided with a sample absorption pad;
  when the cover portion seals off the tube portion, a top of the first chamber communicates with a top of the second chamber, and the first end of the biochemical chromatographic test strip is close to an inner bottom surface of the cover portion.

Preferably, a bottom of the second chamber may be spaced apart from a bottom of the first chamber.

Preferably, the tube body may further include a third chamber, and a bottom of the third chamber may be spaced apart from a bottom of the first chamber; and when the cover portion seals off the tube portion, the top of the first chamber and the top of the second chamber may communicate with the top of the third chamber.

Preferably, a distance between the bottom of the third chamber and the bottom of the first chamber may be at least 3 mm.

Preferably, when the limit unit is subjected to contact conductive heating by a biochemical reaction instrument, the first chamber or the third chamber may contact a heat source of the biochemical reaction instrument.

Preferably, the third chamber may be located at an outer side of the first chamber; and/or, the third chamber may be located at an inner side of the first chamber.

Preferably, an axis of the third chamber may be collinear with or parallel to an axis of the first chamber.

Preferably, the bottom of the third chamber and a top of the limit unit may be in the same horizontal plane; or, a bottom of the third chamber may be located at an upper side of the top of the limit unit.

Preferably, the limit unit may at least partially surround an outer side of the tube body.

Preferably, the tube portion may further include:

a first fitting member provided on a circumferential surface of an inner wall of the tube body;

the cover portion may include:

a second fitting member provided on a circumferential surface of an outer wall of the cover portion; and the second fitting member can be connected to the tube portion, such that the cover portion seals off the tube portion; or, the second fitting member can be connected to the first fitting member, such that the cover portion is fitted with the tube portion and seals off the tube portion.

Preferably, there may be a plurality of first fitting members, and the plurality of first fitting members may be arranged along an axial direction of the tube portion;

there may be a plurality of second fitting members, and the plurality of second fitting members may be arranged along an axial direction of the cover portion; and a second fitting member located at the lowermost side of the cover portion may be at least connected to a first fitting member located at the uppermost side of the tube portion.

Preferably, the biochemical reaction test strip tube may further include:

a connecting member; and both ends of the connecting member may be connected to the tube portion and the cover portion, respectively.

Preferably, the cover portion may include:

an auxiliary member provided on the outer wall of the cover portion; and when the cover portion seals off the tube portion, the auxiliary member protrudes from the tube portion.

Preferably, a thickness of the auxiliary member may be smaller than a thickness of a top of the cover portion; or the auxiliary member may have a thickness smaller than or equal to 0.4 mm.

Preferably, the cover portion may include:

a drainage member with a tapered longitudinal section; and a tip of the drainage member may be aligned with the first chamber.

Preferably, the cover portion may include:

a hollow member, which is provided inside the cover portion in a penetrating manner and includes:

a first opening element provided at an upper end of the hollow member; and a second opening element provided at a lower end of the hollow member; and a sealing member, which is configured to seal off the hollow member and includes:

a first sealing element configured to seal off the first opening element; and a second sealing element configured to seal off the second opening element.

Preferably, when the sealing member seals off the hollow member, the first sealing element may not contact the second sealing element; or the first sealing element may destroy the second sealing element.

Preferably, the hollow member may include:

a third fitting member provided on a circumferential surface of an inner wall of the hollow member; and the sealing member may include:

a fourth fitting member provided on a circumferential surface of an outer wall of the first sealing element; where the third fitting member can be connected to the fourth fitting member, such that the first sealing element seals off the first opening element.

Preferably, the biochemical reaction test strip tube may further include:

a metal warm-bath instrument configured to subject a biochemical reaction solution in the biochemical reaction test strip tube to contact conductive heating.

Preferably, the biochemical chromatographic test strip may be any one from the group consisting of an immunochromatographic test strip, a dry biochemical test strip, a dry chemical test strip, and an enzyme electrode test strip.

In a second aspect of the present disclosure, a biochemical reaction kit is provided, including:

the biochemical reaction test strip tube described above; and a biochemical reaction reagent placed in the first chamber;

where when the cover portion seals off the tube portion, the biochemical reaction reagent in the first chamber completes a biochemical reaction; and then the biochemical reaction test strip tube is flipped at a specified angle, such that a reaction solution in the first chamber is absorbed by the sample absorption pad of the biochemical chromatographic test strip.

Preferably, the biochemical reaction reagent may be a late-PCR gene amplification reagent, a TMA/NASBA gene amplification reagent, an RPA gene amplification reagent, or an LAMP gene amplification reagent.

In a third aspect of the present disclosure, a gene amplification kit is provided, including:

the biochemical reaction test strip tube described above;

a biochemical reaction reagent; and a functional reaction reagent;

where one of the biochemical reaction reagent and the functional reaction reagent is placed inside the first chamber, and the other one of the biochemical reaction reagent and the functional reaction reagent is placed inside the third chamber;

when the cover portion seals off the tube portion and a biochemical reaction proceeds, the biochemical reaction reagent contacts a heat source and the functional reaction reagent does not contact the heat source; and after the biochemical reaction reagent completes the biochemical reaction under heat, the biochemical reaction test strip tube is flipped at a specified angle, such that the functional reaction reagent is mixed with a reaction product obtained after the biochemical reaction to obtain a mixed solution, and the mixed solution is absorbed by the sample absorption pad of the biochemical chromatographic test strip.

In a fourth aspect of the present disclosure, a method for using the biochemical reaction test strip tube described above is provided, including:

sealing off the tube portion by the cover portion to complete a biochemical reaction of the biochemical reaction reagent in the first chamber; and flipping the biochemical reaction test strip tube at a specified angle, such that a reaction solution in the first chamber is absorbed by the sample absorption pad of the biochemical chromatographic test strip.

In a fifth aspect of the present disclosure, a method for using the biochemical reaction test strip tube described above is provided, including:

placing one of a biochemical reaction reagent and a functional reaction reagent inside the first chamber, and placing the other one of the biochemical reaction reagent and the functional reaction reagent inside the third chamber;

sealing off the tube portion by the cover portion to complete a biochemical reaction, where the biochemical reaction reagent contacts a heat source and the functional reaction reagent does not contact the heat source;

after the biochemical reaction reagent completes the biochemical reaction under heat, flipping a biochemical reaction test tube at a specified angle, such that the functional reaction reagent is mixed with a reaction product obtained after the biochemical reaction to obtain a mixed solution, and the mixed solution is absorbed by the sample absorption pad of the biochemical chromatographic test strip.

Compared with the prior art, the above technical solutions adopted by the present disclosure have the following technical effects:

In the biochemical reaction test strip tube of the present disclosure, different chambers are provided in the closed test tube, such that a biochemical reaction solution in one chamber is directly detected on a biochemical chromatographic test strip in another chamber, which avoids the solution leakage; and different chambers are provided at different heights, such that only the chamber holding a biochemical reaction reagent is heated in actual use.

Reference numerals: tube portion: 10; tube body: 11; limit unit: 12; first chamber: 13; second chamber: 14; third chamber: 15; biochemical chromatographic test strip: 16; first fitting member: 17; cover portion: 20; drainage member: 21; second fitting member: 18; connecting member: 30; auxiliary member: 40; hollow member: 50; first opening element: 51; second opening element: 52; third fitting member: 53; sealing member: 60; first sealing element: 61; second sealing element: 62; fourth fitting member: 63; limiting part: 611; destroying part: 612; and metal warm-bath instrument: 70.

DETAILED DESCRIPTION

The technical solutions in the examples of the present disclosure are clearly and completely described below with reference to the accompanying drawings in the examples of the present disclosure. Apparently, the described examples are merely a part rather than all of the examples of the present disclosure. All other examples obtained by a person of ordinary skill in the art based on the examples of the present disclosure without creative efforts shall fall within the protection scope of the present disclosure.

It should be noted that the examples in the present disclosure or features in the examples may be combined in a non-conflicting manner.

The present disclosure is further described below with reference to the accompanying drawings and specific examples, but the present disclosure is not limited thereto.

Example 1

Figure 1:
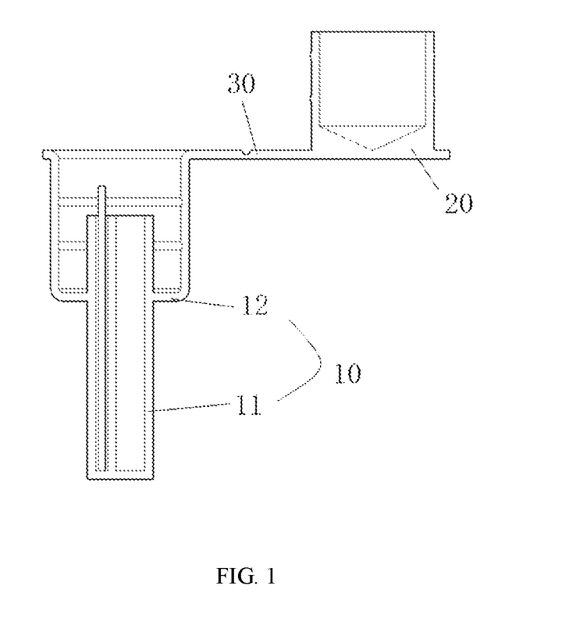
FIG. 1 is a schematic cross-sectional view of a biochemical reaction test strip tube according to an exemplary example of the present disclosure (the tube portion is not sealed off by the cover portion).
Figure 2:
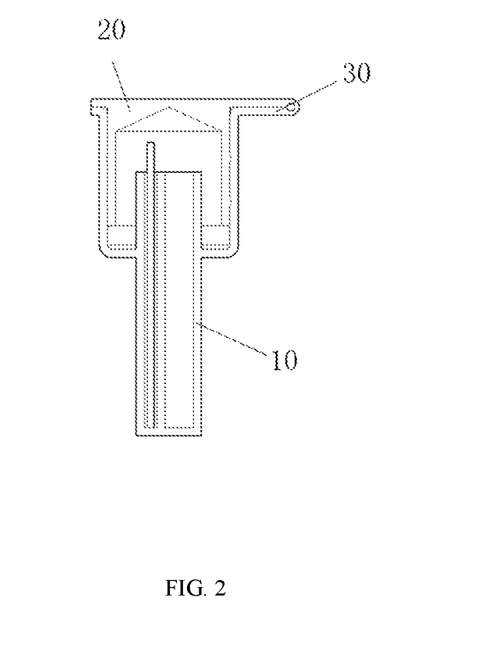
FIG. 2 is a schematic cross-sectional view of a biochemical reaction test strip tube according to an exemplary example of the present disclosure (the tube portion is sealed off by the cover portion).

According to an exemplary example of the present disclosure, as shown in FIG. 1 and FIG. 2, a biochemical reaction test strip tube includes a tube portion 10 and a cover portion 20, and the tube portion 10 includes a tube body 11, a limit unit 12, and a biochemical chromatographic test strip 16. The limit unit 12 is provided on an outer wall of the tube body 11; the tube body 11 includes a first chamber 13 and a second chamber 14; and the biochemical chromatographic test strip 16 is placed in the second chamber 14. When the cover portion 20 seals off the tube portion 10, a top of the first chamber 13 communicates with a top of the second chamber 14.

A first end of the biochemical chromatographic test strip 16 is provided with a sample absorption pad, and when the cover portion 20 seals off the tube portion 10, the first end of the biochemical chromatographic test strip 16 is close to an inner bottom surface of the cover portion 20.

The first chamber 13 is provided for a biochemical reaction reagent or a biochemical reaction solution; and after the biochemical reaction in the first chamber 13 is completed, the biochemical reaction test strip tube is flipped at a specified angle, such that the reaction solution contacts the sample absorption pad of the biochemical chromatographic test strip 16.

The biochemical reaction reagent includes, but is not limited to, an NAA reagent and a gene amplification reagent.

The biochemical chromatographic test strip 16 may be any one from the group consisting of an immunochromatographic test strip, a dry biochemical test strip, a dry chemical test strip, and an enzyme electrode test strip. The reaction solution, after being absorbed by the sample absorption pad of the biochemical chromatographic test strip 16, can chromatographically flow to a reaction zone automatically such that a reaction is completed and a detection signal is displayed.

The second chamber 14 is located at an outer side of the first chamber 13; the second chamber 14 is located between an inner wall of the tube body 11 and an outer wall of the first chamber 13; and the second chamber 14 is in a regular shape (such as a circular chamber, a rectangular chamber, and a trapezoidal chamber) or an irregular shape. In this case, an axis of the second chamber 14 is parallel to an axis of the first chamber 13.

A bottom of the second chamber 14 may be spaced apart from a bottom of the first chamber 13. With this arrangement, a height difference can be formed, and the height difference can lead to a temperature difference during temperature control.

A distance between the bottom of the third chamber 15 and the bottom of the first chamber 13 may be at least 3 mm.

In order to further improve the display effect of a biochemical reaction, the tube body 11 further includes a third chamber 15; and a bottom of the third chamber 15 is spaced apart from the bottom of the first chamber 13, that is, a distance between the bottom of the third chamber 15 and the horizontal plane is greater than a distance between the bottom of the first chamber 13 and the horizontal plane.

The third chamber 15 is provided to hold a functional reaction reagent.

The functional reaction reagent includes, but is not limited to, a degrading enzyme, a lysis solution, a probe, a buffer, a diluent, and the like, or reagents for subsequent reactions after the biochemical reaction is completed.

A distance between the bottom of the third chamber 15 and the horizontal plane is greater than a distance between the bottom of the first chamber 13 and the horizontal plane.

A distance between the bottom of the third chamber 15 and the bottom of the first chamber 13 may be at least 3 mm.

The third chamber 15 is located at an outer side of the first chamber 13; the third chamber 15 is located between the inner wall of the tube body 11 and the outer wall of the first chamber 13; and the third chamber 15 is an annular chamber, that is, the third chamber 15 surrounds a circumferential surface of the outer wall of the first chamber 13. In this case, an axis of the third chamber 15 is collinear with the axis of the first chamber 13.

Correspondingly, the third chamber 15 may be located at an inner side of the first chamber 13; and the third chamber 15 is an annular chamber, that is, the third chamber 15 surrounds a circumferential surface of an inner wall of the first chamber 13. In this case, an axis of the third chamber 15 is collinear with the axis of the first chamber 13.

In another implementation of this example, the third chamber 15 is located at an outer side of the first chamber 13; the third chamber 15 is located between the inner wall of the tube body 11 and the outer wall of the first chamber 13; and the third chamber 15 is a circular chamber, that is, a circumferential surface of the outer wall of the third chamber 15 is tangential to a circumferential surface of the outer wall of the first chamber 13. In this case, an axis of the third chamber 15 is parallel to the axis of the first chamber 13. There may be a plurality of third chambers 15, and the plurality of third chambers 15 are surroundingly provided on a circumferential surface of the outer wall of the first chamber 13 with the first chamber 13 as a center.

Correspondingly, the third chamber 15 may be located at an inner side of the first chamber 13; and the third chamber 15 is a circular chamber, that is, a circumferential surface of the outer wall of the third chamber 15 is tangential to a circumferential surface of the inner wall of the first chamber 13. In this case, an axis of the third chamber 15 is parallel to the axis of the first chamber 13. There may be a plurality of third chambers 15, and the plurality of third chambers 15 are surroundingly provided on a circumferential surface of the inner wall of the first chamber 13 with the first chamber 13 as a center.

In the above structure, the third chamber 15 and the first chamber 13 may be provided integrally or separately. In the case where the third chamber 15 and the first chamber 13 are provided separately, the third chamber 15 is removably provided at an outer side of the first chamber 13, and a removable manner includes, but is not limited to, a snap connection.

The limit unit 12 at least partially surrounds the tube body 11, that is, a connecting side of the limit unit 12 with the tube body 11 is in an arc shape with at least an acute central angle. Specifically, the limit unit 12 may be a full skirt, a half skirt, or a quarter skirt.

A distance between the top of the limit unit 12 and the bottom of the third chamber 15 may be 0, that is, the top of the limit unit 12 and the bottom of the third chamber 15 are in the same horizontal plane; or, a distance between the top of the limit unit 12 and the bottom of the third chamber 15 may be greater than 0, that is, in a vertical direction, the limit unit 12 is located at a lower side of the third chamber 15.

The limit unit 12 is a symmetrical cylinder or cone, which can be inserted into the biochemical reaction instrument at any angle for fixing.

Or, the limit unit 12 is an asymmetrical cylinder, which can only be inserted into the biochemical reaction instrument at a single angle for fixing.

When the limit unit 12 is subjected to contact conductive heating by a biochemical reaction instrument, a solution (with a biochemical reaction reagent) at the bottom of the first chamber 13 is subjected to contact conductive heating, while a solution (with a functional reaction reagent) at the bottom of the third chamber 15 is not subjected to contact conductive heating; or, a solution (with a biochemical reaction reagent) at the bottom of the third chamber 15 is subjected to contact conductive heating, while a solution (with a functional reaction reagent) at the bottom of the first chamber 13 is not subjected to contact conductive heating.

The cover portion 20 includes a drainage member 21, which is provided on an inner top surface of the cover portion 20 and has a tapered longitudinal section. When the cover portion 20 seals off the tube portion 10, a tip of the drainage member 21 is aligned with the first chamber 13. The drainage member 21 is provided to achieve the following purpose: during the progress of a biochemical reaction, a reaction solution in the first chamber 13 is heated and evaporated to form water vapor which is condensed on the cover portion 20, and under the guidance of the drainage member 21, condensed droplets return to the third chamber 15, which avoids that the condensed droplets directly contact the biochemical chromatographic test strip 16 or drip onto the biochemical chromatographic test strip 16.

In order to improve the sealing effect between the tube portion 10 and the cover portion 20, the tube portion 10 and the cover portion 20 are provided with a first fitting member 17 and a second fitting member 22, respectively.

Figure 3:
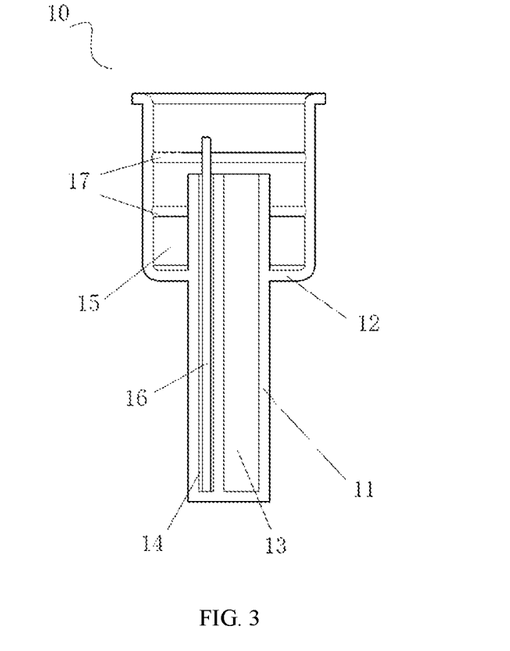
FIG. 3 is a schematic cross-sectional view of a tube portion of a biochemical reaction test strip tube according to an exemplary example of the present disclosure.

As shown in FIG. 3, the first fitting member 17 is provided on a circumferential surface of the inner wall of the tube body 11, and there may be at least one first fitting member 17.

Figure 4:
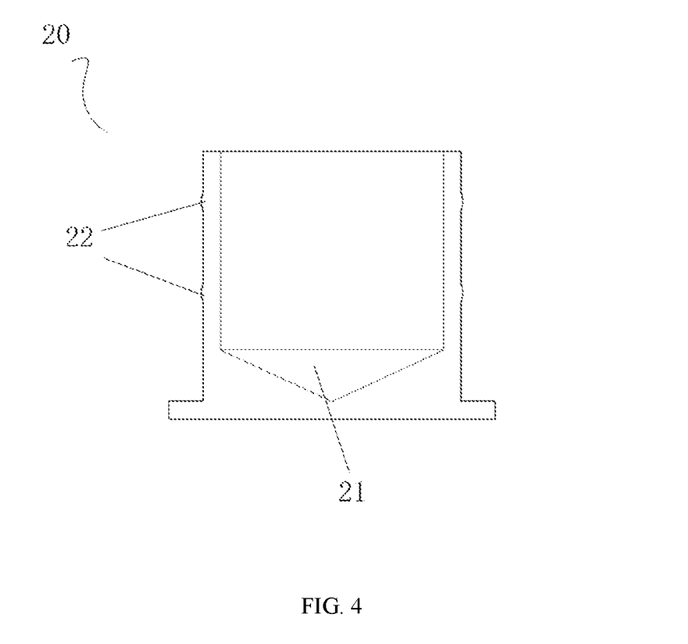
FIG. 4 is a schematic cross-sectional view of a cover portion of a biochemical reaction test strip tube according to an exemplary example of the present disclosure.

As shown in FIG. 4, the second fitting member 22 is provided on a circumferential surface of the outer wall of the cover portion 20, and there may be at least one second fitting member 22.

When the cover portion 20 seals off the tube portion 10, the second fitting member 22 is connected to the first fitting member 17, such that the cover portion 20 and the tube portion 10 fit with each other to improve the sealing effect of the cover portion 20 for the tube portion 10.

The first fitting member 17 is a groove (or a sealing groove), and the second fitting member 22 is a protrusion (or a raised sealing ring); or the first fitting member 17 is a protrusion (or a raised sealing ring), and the second fitting member 22 is a groove (or a sealing groove).

There may be a plurality of first fitting members 17, and the first fitting members 17 are arranged along an axial direction of the tube portion 10. Similarly, there may be a plurality of second fitting members 22, and the second fitting members 22 are arranged along an axial direction of the cover portion 20.

The first fitting members 17 and the second fitting members 22 may be connected in a one-to-one correspondence. Specifically, when the cover portion 20 seals off the tube portion 10, a first fitting member 17 at the lowermost side of the tube portion 10 is connected to a second fitting member 22 at the lowermost side of the cover portion 20; and a first fitting member 17 at the uppermost side of the tube portion 10 is connected to a second fitting member 22 at the uppermost side of the cover portion 20. In this case, a relatively-large external force is required to remove the cover portion 20 to expose an inner chamber of the tube portion 10.

The first fitting members 17 and the second fitting members 22 may not be connected in a one-to-one correspondence. For example, when the cover portion 20 seals off the tube portion 10, a first fitting member 17 at the uppermost side of the tube portion 10 is connected to a second fitting member 22 at the lowermost side of the cover portion 20. In this case, the cover portion 20 can be easily removed to expose an inner chamber of the tube portion 10.

It can be known from the above that, in order to allow the cover portion 20 to seal off the tube portion 10, the first fitting member 17 at the uppermost side of the tube portion 10 is at least connected to the second fitting member 22 at the lowermost side of the cover portion 20.

The first fitting members 17 and the second fitting members 22 may not be fitted and connected. For example, in the case where the cover portion 20 seals off the tube portion 10, the first fitting member 17 at the uppermost side of the tube portion 10 is not fitted and connected with the second fitting member 22 at the lowermost side of the cover portion 20, and the second fitting member 22 is only connected to the tube portion 10, which can achieve a sealing effect.

In order to ensure a one-to-one correspondence between the tube portion 10 and the cover portion 20, a connecting member 30 is also provided to connect the tube portion 10 and the cover portion 20. Specifically, a first end of the connecting member 30 is connected to an outer wall of a top of the tube portion 10, and a second end of the connecting member 30 is connected to an outer wall of a top of the cover portion 20.

The connecting member 30 may be a connecting stranded strip.

As shown in FIG. 2, when the cover portion 20 seals off the tube portion 10, except for the folded connecting member 30, an outer edge of a top of the cover portion 20 does not extend beyond any part of a top edge of the tube portion 10.

Example 2

In this example, a specific implementation of the present disclosure is provided, which is an improved implementation for Example 1 and can facilitate the removal of the cover portion 20.

Figure 5:
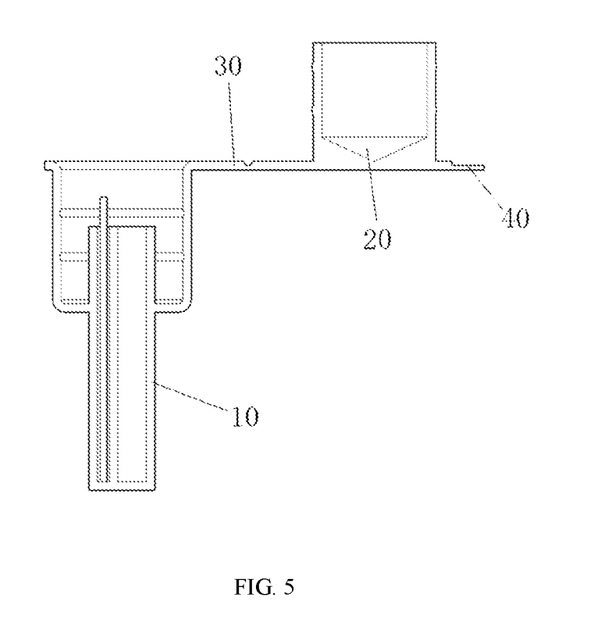
FIG. 5 is a schematic cross-sectional view of a biochemical reaction test strip tube according to a specific implementation of the present disclosure (the tube portion is not sealed off by the cover portion).
Figure 6:
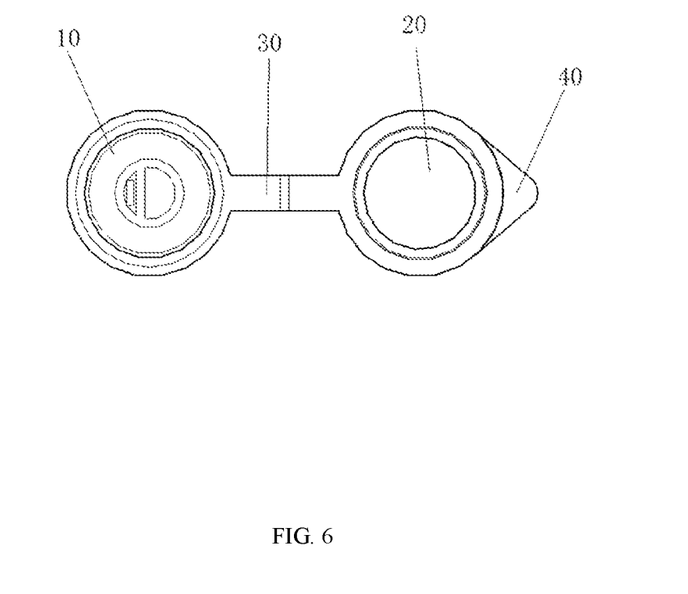
FIG. 6 is a schematic top view of a biochemical reaction test strip tube according to a specific implementation of the present disclosure.

As shown in FIG. 5 and FIG. 6, a biochemical reaction test strip tube includes a tube portion 10, a cover portion 20, a connecting member 30, and an auxiliary member 40. Structures of and a connection relationship among the tube portion 10, the cover portion 20, and the connecting member 30 are basically the same as that in Example 1, which will not be repeated here.

The auxiliary member 40 is provided on an outer wall of the cover portion 20; and when the cover portion 20 seals off the tube portion 10, the auxiliary member 40 protrudes from the tube portion 10. That is, the auxiliary member 40 is a protrusion that extends out from a top edge of the tube portion 10 along an outer edge of a top of the cover portion 20 at a specified length.

The auxiliary member 40 is provided at a symmetrical side relative to the connecting member 30.

A thickness of the auxiliary member 40 is smaller than a thickness of the top of the cover portion 20.

The auxiliary member 40 may have a thickness smaller than or equal to 0.04 mm.

Example 3

In this example, a specific implementation of the present disclosure is provided, which is an improved implementation for Example 1 and can facilitate the addition of a solution into the third chamber 15.

Figure 7:
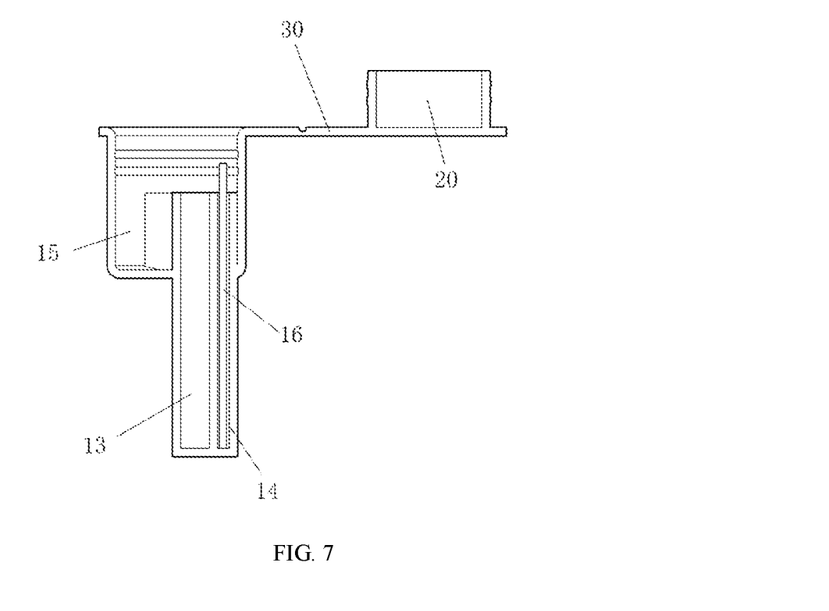
FIG. 7 is a schematic cross-sectional view of a biochemical reaction test strip tube according to a specific implementation of the present disclosure (the tube portion is not sealed off by the cover portion).
Figure 8:
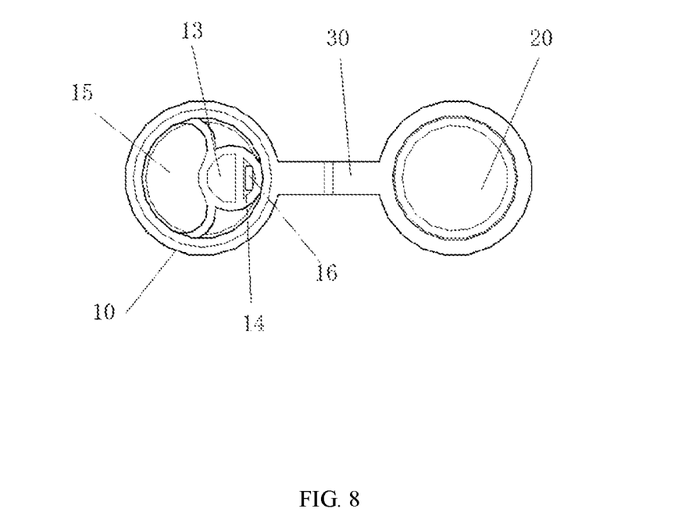
FIG. 8 is a schematic top view of a biochemical reaction test strip tube according to a specific implementation of the present disclosure.

As shown in FIG. 7 and FIG. 8, a biochemical reaction test strip tube includes a tube portion 10, a cover portion 20, and a connecting member 30. Structures of and a connection relationship between the cover portion 20 and the connecting member 30 are basically the same as that in Example 1, which will not be repeated here.

As shown in FIG. 7 and FIG. 8, in the tube portion 10, the third chamber 15 is located between the outer wall of the tube body 11 and the inner wall of the limit unit 12, and an axis of the third chamber 15 is parallel to an axis of the first chamber 13, that is, the first chamber 13 is provided at an eccentric position of a bottom surface of the third chamber 15.

Specifically, an outer wall of the first chamber 13 at one side is far away from an inner wall of the limit unit 12 at a corresponding side, and an outer wall of the first chamber 13 at the other side is close to an inner wall of the limit unit 12 at a corresponding side, which makes a radial size of the third chamber 15 increase. Therefore, a tip of a pipette tip can be inserted deeply into the third chamber 15, which allows a solution to enter the third chamber 15 smoothly and prevents the solution from entering the first chamber 13 due to an improper operation of an operator.

Example 4

In this example, a specific implementation of the present disclosure is provided, which is an improved implementation for Example 1 and can further reduce the probability of contamination to the biochemical reaction test strip tube.

Figure 9:
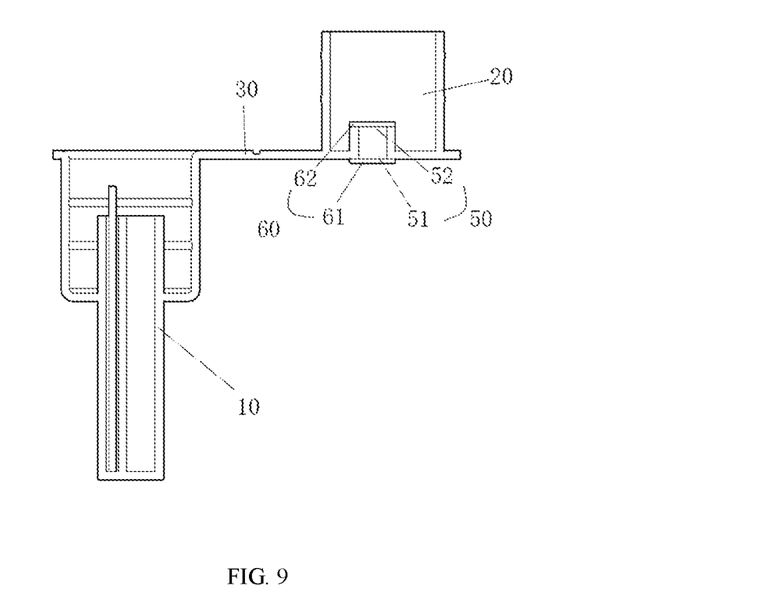
FIG. 9 is a schematic cross-sectional view of a biochemical reaction test strip tube according to a specific implementation of the present disclosure (the tube portion is not sealed off by the cover portion).
Figure 10:
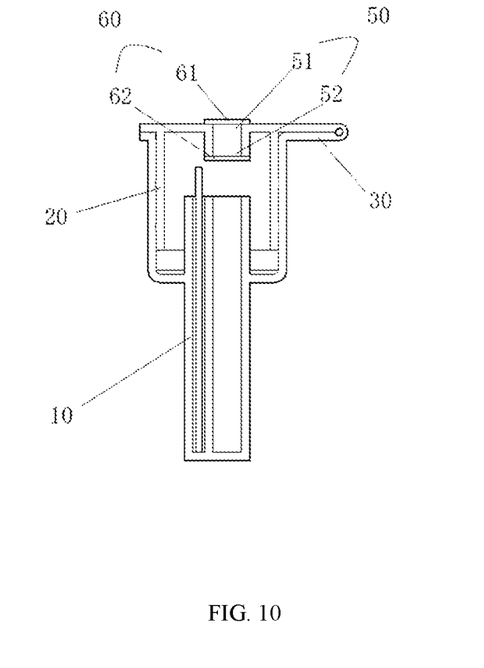
FIG. 10 is a schematic cross-sectional view of a biochemical reaction test strip tube according to a specific implementation of the present disclosure (the tube portion is sealed off by the cover portion).

As shown in FIG. 9 and FIG. 10, a biochemical reaction test strip tube includes a tube portion 10, a cover portion 20, and a connecting member 30. Structures of and a connection relationship between the tube portion 10 and the connecting member 30 are basically the same as that in Example 1, which will not be repeated here.

As shown in FIG. 9 and FIG. 10, on the basis of Example 1, the cover portion 20 further includes a hollow member 50 and a sealing member 60, where the hollow member 50 is provided inside the cover portion 20 in a penetrating manner and the sealing member 60 seals off the hollow member 50.

The hollow member 50 includes a first opening element 51 provided at an upper end of the hollow member 50, such that a solution enters an interior of the hollow member 50 from an outer side of the cover portion 20 through the first opening element 51.

Correspondingly, the sealing member 60 includes a first sealing element 61, which seals off the first opening element 51.

Specifically, the first sealing element 61 is a sealing film or a sealing film with a sticker. During operation, the first sealing element 61 is removed, a biochemical reaction solution is added into the hollow member 50, and then the first sealing element 61 is used to seal off the first opening element 51.

On the basis of the above structure, in order to further improve the operation efficiency, the hollow member 50 further includes a second opening element 52 provided at a lower end of the hollow member 50, and the sealing member 60 further includes a second sealing element 62 configured to seal off the second opening element 62.

Specifically, the second sealing element 62 is an easily-destroyed sealing element, such as a sealing film, an aluminum foil with a sealing and pasting material, or other film materials. In the first operation, the first sealing element 61 is removed, a biochemical reaction solution is added into the hollow member 50, and then the first sealing element 61 is used to seal off the first opening element 51; and in the second operation, the first sealing element 61 is removed, and a tool is used by an operator to sequentially pass through the first opening element 51 and the second opening element 52 and then destroy the second sealing element 62, such that the biochemical reaction solution inside the hollow member 50 enters an interior of the tube body 11, and finally the first sealing element 61 is used to seal off the first opening element 51.

Example 5

In this example, a specific implementation of the present disclosure is provided, which is an improved implementation for Example 1 and can further reduce the probability of contamination to the biochemical reaction test strip tube.

Figure 11:
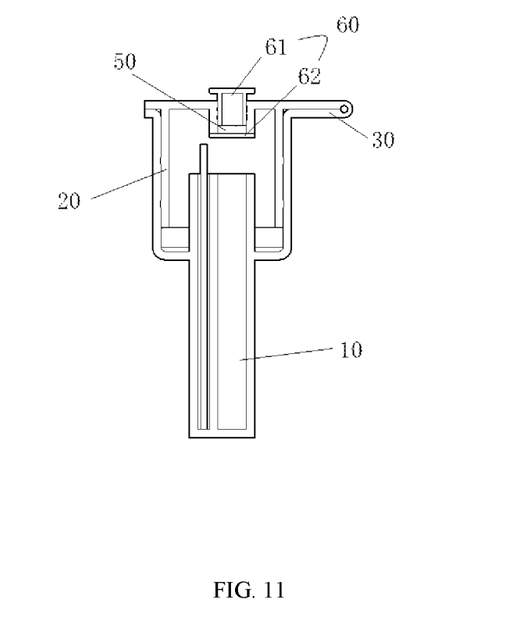
FIG. 11 is a schematic cross-sectional view of a biochemical reaction test strip tube according to a specific implementation of the present disclosure (the tube portion is sealed off by the cover portion).

As shown in FIG. 11, a biochemical reaction test strip tube includes a tube portion 10, a cover portion 20, and a connecting member 30. Structures of and a connection relationship between the tube portion 10 and the connecting member 30 are basically the same as that in Example 1, which will not be repeated here.

As shown in FIG. 11, on the basis of Example 1, the cover portion 20 further includes a hollow member 50 and a sealing member 60, where the hollow member 50 is provided inside the cover portion 20 in a penetrating manner and the sealing member 60 seals off the hollow member 50.

The hollow member 50 includes a first opening element 51 provided at an upper end of the hollow member 50 and a second opening element 52 provided at a lower end of the hollow member 50.

Correspondingly, the sealing member 60 includes a first sealing element 61 to seal off the first opening element 51 and a second sealing element 62 to seal off the second opening element 52, and when the first sealing element 61 completely seals off the first opening element 51, the first sealing element 61 destroys the second sealing element 62.

The first sealing element 61 includes a limiting part 611 and a destroying part 612, and the destroying part 612 is provided at a lower end of the limiting part 611. An inner diameter of the limiting part 611 is greater than an inner diameter of the hollow member 50, and an inner diameter of the destroying part 612 is less than or equal to an inner diameter of the hollow member 50. When the first sealing element 61 completely seals off the first opening element 51, a bottom end of the destroying part 612 destroys the second sealing element 62.

Specifically, the limiting part 611 is a cover plate, and the destroying part 612 is a hollow tube.

The limiting part 611 and the destroying part 612 are movably connected, that is, when a specified operation (such as opening) is applied to the limiting part 611, a biochemical reaction component or solution can be added to the destroying part 612.

Specifically, the limiting part 611 and the destroying part 612 may be in nested connection, threaded connection, snap connection, etc., for example, the limiting part 611 and the destroying part 612 are connected in the same manner as that between the cover portion 20 and the tube portion 10.

Specifically, the second sealing element 62 is an easily-destroyed sealing element, such as a sealing film, an aluminum foil with a sealing and pasting material, or other film materials.

In order to improve the sealing effect between the hollow member 50 and the sealing member 60, the hollow member 50 and the sealing member 60 are provided with a third fitting member 53 and a fourth fitting member 63, respectively.

Figure 12:
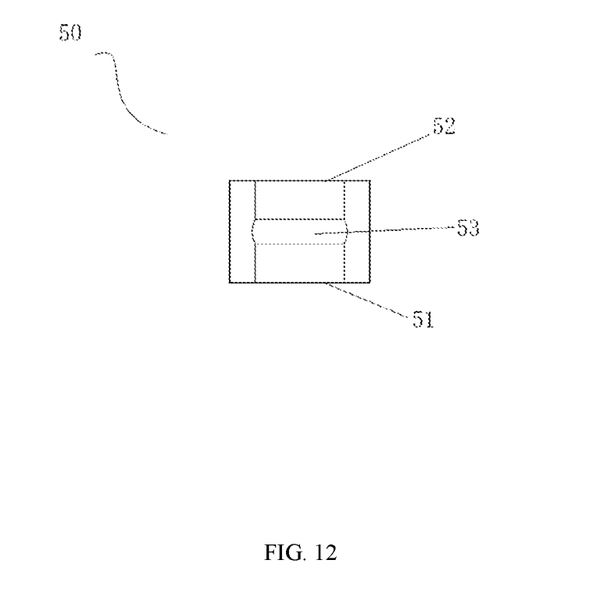
FIG. 12 is a schematic cross-sectional view of a hollow member of a biochemical reaction test strip tube according to a specific implementation of the present disclosure.

As shown in FIG. 12, the third fitting member 53 is provided on a circumferential surface of an inner wall of the hollow member 50, and there may be at least one third fitting member 53.

Figure 13:
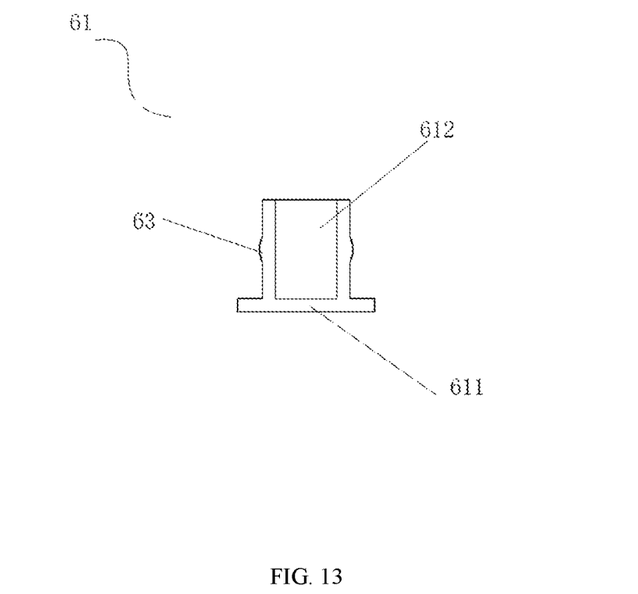
FIG. 13 is a schematic cross-sectional view of a first sealing element of a biochemical reaction test strip tube according to a specific implementation of the present disclosure.

As shown in FIG. 13, the fourth fitting member 63 is provided on a circumferential surface of an outer wall of the first sealing element 61, and there may be at least one fourth fitting member 63.

When the first sealing element 61 seals off the first opening element 51, the fourth fitting member 63 is connected to the third fitting member 53, such that the first sealing element 61 and the hollow member 50 fit with each other to improve the sealing effect of the first sealing element 61 for the first opening element 51.

The third fitting member 53 is a groove (or a sealing groove), and the fourth fitting member 63 is a protrusion (or a raised sealing ring); or the third fitting member 53 is a protrusion (or a raised sealing ring), and the fourth fitting member 63 is a groove (or a sealing groove).

There may be a plurality of third fitting members 53, and the third fitting members 53 are arranged along an axial direction of the hollow member 50. Similarly, there may be a plurality of fourth fitting members 63, and the fourth fitting members 63 are arranged along an axial direction of the first sealing element 61.

The third fitting members 53 and the fourth fitting members 63 may be connected in a one-to-one correspondence. Specifically, a third fitting member 53 at the lowermost side of the hollow member 50 is connected to a fourth fitting member 63 at the lowermost side of the first sealing element 61; and the third fitting member 53 at the uppermost side of the hollow member 50 is connected to a fourth fitting member 63 at the uppermost side of the first sealing element 61. In this case, the first sealing element 61 destroys the second sealing element 62.

The third fitting members 53 and the fourth fitting members 63 may not be connected in a one-to-one correspondence. For example, a third fitting member 53 at the uppermost side of the hollow member 50 is connected to a fourth fitting member 63 at the lowermost side of the first sealing element 61. In this case, the first sealing element 61 does not destroy the second sealing element 62.

When the biochemical reaction test strip tube of this example is used, the limiting part 611 of the first sealing element 61 can be opened, and a biochemical reaction component or solution can be placed inside the destroying part 612; the first sealing element 61 is inserted into the hollow member 50 through the first opening element 51 and destroys the second sealing element 62; and the biochemical reaction component or solution in the destroying part 612 is mixed with a solution inside the tube body 11 to further achieve a biochemical reaction. For example, a nucleic acid-degrading enzyme is placed in the destroying part 612 to degrade an NAA product inside the biochemical reaction test strip tube.

Example 6

In this example, a specific implementation of the present disclosure is provided, which is an extended implementation for Examples 1 to 5.

Figure 14:
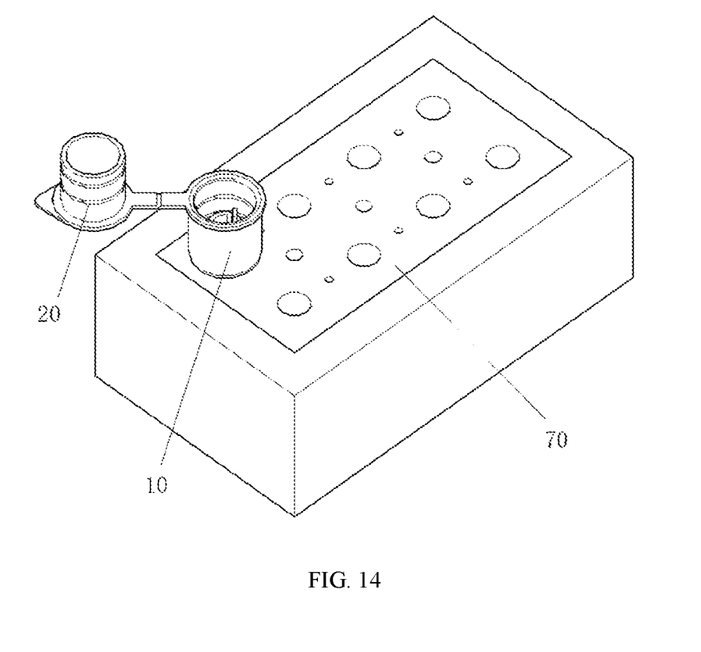
FIG. 14 is schematic diagram of a biochemical reaction test strip tube with a metal warm-bath instrument according to a specific implementation of the present disclosure.

As shown in FIG. 14, the biochemical reaction test strip tube also includes a metal warm-bath instrument 70 that achieves contact temperature conduction control for a solution inside the biochemical reaction test strip tube, where a specified temperature value can be set, such that a temperature can be stably kept at a specified value according to set conditions or can cyclically change among multiple temperature values.

Example 7

In this example, the use and use method of the biochemical reaction test strip tube of Examples 1 to 5 are provided.

A biochemical reaction kit is provided, which at least includes the biochemical reaction test strip tube and a biochemical reaction reagent. The biochemical reaction reagent is placed in the first chamber 13 of the tube body 11.

In use, when the cover portion 20 seals off the tube portion 10, the biochemical reaction reagent in the first chamber 13 completes a biochemical reaction, then the biochemical reaction test strip tube is flipped at a specified angle, and a reaction solution in the first chamber 13 is absorbed by the sample absorption pad of the biochemical chromatographic test strip 16, thereby starting the chromatographic flow of the reaction solution on the biochemical chromatographic test strip and the display of a detection signal of the test strip for the reaction solution.

Example 8

In this example, the use and use method of the biochemical reaction test strip tube of Examples 1 to 5 are provided.

A gene amplification kit is provided, which at least includes a biochemical reaction test strip tube, a biochemical reaction reagent, and a functional reaction reagent. The biochemical reaction reagent is placed in the first chamber 13 of the tube body 11 and the functional reaction reagent is placed in the third chamber 15 of the tube body 11; or, the biochemical reaction reagent is placed in the third chamber 15 of the tube body 11 and the functional reaction reagent is placed in the first chamber 13 of the tube body 11.

The thermal sensitivity of the functional reaction reagent is different from that of the biochemical reaction reagent.

Specifically, the biochemical reaction reagent includes, but is not limited to, amplification reagents, such as an NAA reagent, a late-PCR gene amplification reagent, a TMA/NASBA gene amplification reagent, a RPA gene amplification reagent, or a LAMP gene amplification reagent.

Specifically, the functional reaction reagent includes, but is not limited to, a degrading enzyme, a lysis solution, a probe, a buffer, a diluent, and the like, or reagents for subsequent reactions after an amplification reaction is completed.

In a first specific implementation of this example, the biochemical reaction reagent is an NAA reagent, and the functional reaction reagent is a diluent. In this implementation, after the NAA reagent in the first chamber 13 (or the third chamber 15) completes an amplification reaction under heat, the biochemical reaction test strip tube is flipped at a specified angle (for example, the tube is vertically flipped at 180°) and shaken, such that the diluent in the third chamber 15 (or the first chamber 13) is mixed with an amplification product solution in the first chamber 13 (or the third chamber 15) and a resulting mixture is absorbed at a sample absorption point of the biochemical chromatographic test strip (such as an immunochromatographic test strip), which initiates the chromatographic flow of a diluted amplification product solution on the biochemical chromatographic test strip and the display of a detection signal of the immunochromatographic test strip for the amplification product.

In a second specific implementation of this example, the biochemical reaction reagent is a late-PCR gene amplification reagent. In this implementation, the late-PCR gene amplification reagent is placed in the first chamber 13, where the 5' terminus of a primer to polymerize a single-stranded product in the amplification product is labeled with a small molecule J1, an upper end of a probe capable of binding to the single-stranded product is labeled with a molecule J2, and the J1/J2 can be used to form a sandwich detection method with the labeled and coated ligand of the biochemical chromatographic test strip (such as an immunochromatographic test strip).

In a third specific implementation of this example, the biochemical reaction reagent is an LAMP gene amplification reagent, where the 5' terminus of loop primers LF/LB in the reagent are labeled with small molecules J1/J2, respectively, and the J1/J2 can be used to form a sandwich detection method with the labeled and coated ligand of the biochemical chromatographic test strip (such as an immunochromatographic test strip).

The above examples are merely preferred examples of the present disclosure, which are not intended to limit the implementation and protection scope of the present disclosure. It should be noted by those skilled in the art that all equivalent replacements and obvious changes made by using the description of the present disclosure and the content of the drawings should be included in the protection scope of the present disclosure.

What is claimed is:

1. A biochemical reaction test strip tube comprising a tube portion and a cover portion wherein the cover portion comprises:
   a cover portion lowermost side;
   a cover portion inner bottom surface; and
   a cover portion outer wall having a cover portion outer wall circumferential surface, and wherein the tube portion comprises:
   a tube body comprising a tube body outer wall, a tube body inner wall, a tube body uppermost side, a first chamber and a second chamber wherein the tube body inner wall comprises a tube body inner wall circumferential surface, and wherein the first chamber has a first chamber top and the second chamber has a second chamber top;
   a limit unit disposed at the tube body outer wall;
   a biochemical chromatographic test strip having a biochemical chromatographic test strip end and disposed in the second chamber, wherein the chromatographic test strip end includes a sample absorption pad;
   a first plurality of fitting members disposed on the tube body inner wall circumferential surface and along an axial direction of the tube portion; and
   wherein
   the cover portion further comprises a second plurality of fitting members disposed on the cover portion outer wall circumferential surface and along an axial direction of the cover portion, wherein either at least one fitting member of the second plurality of fitting members is connectable to the tube portion such that, when connected, the cover portion seals off the tube portion or at least one fitting member of the second plurality of fitting members is connectable to at least one fitting member of the first plurality of fitting members such that, when connected, the cover portion is fitted with the tube portion and seals off the tube portion whereby the first chamber top communicates with the second chamber top, and the biochemical chromatographic test strip end is close to the cover portion inner bottom surface, and one fitting member of the second plurality of fitting members located at the cover portion lowermost side is connected to one fitting member of the first plurality of fitting members located at the tube portion uppermost side.

2. The biochemical reaction test strip tube according to claim 1, wherein the second chamber has a second chamber bottom and the first chamber has a first chamber bottom wherein the second chamber bottom is spaced apart from the first chamber bottom.

3. The biochemical reaction test strip tube according to claim 1, wherein the tube body further comprises a third chamber having a third chamber top and a third chamber bottom spaced apart from the first chamber bottom; and when the cover portion seals off the tube portion, the first chamber top and the second chamber top communicate with the third chamber top; wherein the third chamber bottom is disposed from the first chamber bottom at a distance of at least 3 mm; wherein when the limit unit is subjected to contact conductive heating by a biochemical reaction instrument including a heat source, the first chamber or the third chamber contacts the heat source of the biochemical reaction instrument.

4. The biochemical reaction test strip tube according to claim 3, wherein the first chamber comprises a first chamber outer side and a first chamber inner side and the third chamber is located at the first chamber outer side; and/or, the third chamber is located at the first chamber inner side; wherein the first chamber has a first chamber axis and the third chamber has a third chamber axis collinear with or parallel to the first chamber axis.

5. The biochemical reaction test strip tube according to claim 3, wherein limit unit comprises a limit unit top comprising a limit unit top upper side and wherein the third chamber bottom and the limit unit top are in a horizontal plane; or, the third chamber bottom is located at the limit unit top upper side.

6. The biochemical reaction test strip tube according to claim 1, wherein the limit unit at least partially surrounds the tube body outer wall.

7. The biochemical reaction test strip tube according to claim 1, further comprising: a connecting member comprising a connecting member first end and a connecting member second end, wherein the connecting member first end is connected to the tube portion and the connecting member second end is connected to the cover portion.

8. The biochemical reaction test strip tube according to claim 1, wherein the cover portion further comprises:
   an auxiliary member having a first thickness and disposed on the cover portion outer wall; and when the cover portion seals off the tube portion, the auxiliary member protrudes from the tube portion; wherein the cover portion has a cover portion top having a second thickness wherein the first thickness is smaller than the second thickness; or wherein the second thickness is smaller than or equal to 0.4 mm.

9. The biochemical reaction test strip tube according to claim 1, wherein the cover portion further comprises: a drainage member having a tapered longitudinal section; and a tip aligned with the first chamber.

10. The biochemical reaction test strip tube according to claim 1, wherein the cover portion further comprises:
   a hollow member having an hollow member upper end and a hollow member lower end, the hollow member disposed inside the cover portion in a penetrating manner and comprising: a first opening element disposed at the hollow member upper end; and a second opening element disposed at the hollow member lower end; and a sealing member configured to seal off the hollow member and comprising: a first sealing element configured to seal off the first opening element; and a second sealing element configured to seal off the second opening element.

11. The biochemical reaction test strip tube according to claim 10, wherein when the sealing member seals off the hollow member, either the first sealing element does not contact the second sealing element or the first sealing element destroys the second sealing element.

12. The biochemical reaction test strip tube according to claim 10, wherein the hollow member comprises a hollow member inner wall having a hollow member inner wall circumferential surface, wherein the hollow member further comprises: a third fitting member disposed on the hollow member inner wall circumferential surface; and wherein the sealing member comprises a first sealing element having a first sealing element outer wall having a first sealing element outer wall circumferential surface, wherein the sealing member further comprises: a fourth fitting member disposed on the first sealing element outer wall circumferential surface; wherein the third fitting member is connectable to the fourth fitting member, such that, when connected, the first sealing element seals off the first opening element.

13. The biochemical reaction test strip tube according to claim 3, further comprising:
a metal warm-bath instrument configured to subject a biochemical reaction solution in the biochemical reaction test strip tube to contact conductive heating.

14. The biochemical reaction test strip tube according to claim 1, wherein the biochemical chromatographic test strip is selected from the group consisting of an immunochromatographic test strip, a dry biochemical test strip, a dry chemical test strip, and an enzyme electrode test strip.

15. A biochemical reaction kit, comprising:
the biochemical reaction test strip tube according to claim 1; and
a biochemical reaction reagent placed in the first chamber; wherein the gene amplification kit is configured such that when the cover portion seals off the tube portion, the biochemical reaction reagent in the first chamber completes a biochemical reaction; and after the biochemical reaction is completed, the biochemical reaction test strip tube can be flipped at a specified angle such that a reaction solution in the first chamber is absorbed by the sample absorption pad of the biochemical chromatographic test strip; wherein the biochemical reaction reagent is a late-PCR gene amplification reagent, a TMA/NASBA gene amplification reagent, an RPA gene amplification reagent, or an LAMP gene amplification reagent.

16. A gene amplification kit, comprising:
the biochemical reaction test strip tube according to claim 3;
a biochemical reaction reagent; and
a functional reaction reagent wherein either the biochemical reaction reagent is placed inside the first chamber and the functional reaction reagent is disposed inside the third chamber or the biochemical reaction reagent is disposed inside the third chamber and the functional reagent is disposed inside the first chamber; the gene amplification kit configured such that when the cover portion seals off the tube portion and a biochemical reaction proceeds, the biochemical reaction reagent contacts the heat source and the functional reaction reagent does not contact the heat source; and after the biochemical reaction reagent completes the biochemical reaction under heat, the biochemical reaction test tube can be flipped at a specified angle such that the functional reaction reagent is mixed with a reaction product obtained after the biochemical reaction is completed to obtain a mixed solution, and the mixed solution is absorbed by the sample absorption pad of the biochemical chromatographic test strip.

* * * * *